(12) United States Patent
Peddy et al.

(10) Patent No.: US 9,701,641 B2
(45) Date of Patent: Jul. 11, 2017

(54) ENZALUTAMIDE POLYMORPHIC FORMS AND ITS PREPARATION

(71) Applicant: DR. REDDY'S LABORATORIES LIMITED, Hyderabad (IN)

(72) Inventors: Vishweshwar Peddy, Hyderabad (IN); Rajesham Boge, Hyderabad (IN); Lokeswara Rao Madivada, Mopidevi (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 15/292,696

(22) Filed: Oct. 13, 2016

(65) Prior Publication Data

US 2017/0029380 A1    Feb. 2, 2017

Related U.S. Application Data

(63) Continuation of application No. 14/427,527, filed as application No. PCT/IB2013/058455 on Sep. 11, 2013, now abandoned.

(30) Foreign Application Priority Data

Sep. 11, 2012    (IN) .......................... 3772/CHE/2012

(51) Int. Cl.
 *C07D 233/86*    (2006.01)
(52) U.S. Cl.
 CPC ........ *C07D 233/86* (2013.01); *C07B 2200/13* (2013.01)
(58) Field of Classification Search
 None
 See application file for complete search history.

(56) References Cited

U.S. PATENT DOCUMENTS

| 2002/0009494 A1 | 1/2002 | Curatolo et al. |
| 2006/0079706 A1 | 4/2006 | Parthasaradhi et al. |
| 2007/0254933 A1 | 11/2007 | Jung et al. |
| 2012/0295944 A1 | 11/2012 | Sawyers et al. |

FOREIGN PATENT DOCUMENTS

| WO | 2011/106570 A1 | | 9/2011 |
| WO | WO2011106570 | * | 9/2011 |

OTHER PUBLICATIONS

International Search Report dated Apr. 3, 2014, for corresponding International Patent Application No. PCT/IB2013/058455.
Written Opinion dated Apr. 3, 2014, for corresponding International Patent Application No. PCT/IB2013/058455.
International Preliminary Report on Patentability issued Mar. 17, 2015, for corresponding International Patent Application No. PCT/IB2013/058455.
Non-Final Office Action dated Sep. 9, 2015, mailed by the USPTO, for corresponding U.S. Appl. No. 14/427,527.
Final Office Action dated Mar. 22, 2016, mailed by the USPTO, for corresponding U.S. Appl. No. 14/427,527.
Non-Final Office Action dated Jul. 14, 2016, mailed by the USPTO, for corresponding U.S. Appl. No. 14/427,527.
Center for Drug Evaluation and Research, Clinical Pharmacology and Biopharmaceutics Reviews, May 22, 2012, pp. 1 to 83.
Julie L. Calahan, "Characterization of Amorphous Solid Dispersions of AMG 517 in HPMC-AS Crystallization using Isothermal Microcalorimetry", Apr. 2011, pp. 1 to 128.

* cited by examiner

*Primary Examiner* — Matthew Coughlin
*Assistant Examiner* — Po-Chih Chen
(74) *Attorney, Agent, or Firm* — Pergament & Cepeda LLP; Milagros A. Cepeda; Edward D. Pergament

(57) ABSTRACT

The present application relates to crystalline and amorphous forms of Enzalutamide. The present application further relates to amorphous solid dispersions of Enzalutamide with pharmaceutically acceptable carriers. The present application also relates to a process for the preparation of Form R1 of Enzalutamide.

5 Claims, 4 Drawing Sheets

ENZALUTAMIDE POLYMORPHIC FORMS AND ITS PREPARATION

INTRODUCTION

This application is a Continuation of U.S. patent application Ser. No. 14/427,527, filed Mar. 11, 2015, which is a National Stage Application under 35 U.S.C. §371 of PCT International Application No. PCT/IB2013/058455, filed Sep. 11, 2013, which claims the benefit of Indian Provisional Application No. 3772/CHE/2012, filed Sep. 11, 2012, all of which are hereby incorporated by reference in their entireties.

Aspects of the present application relate to polymorphic forms of enzalutamide which are useful in making pharmaceutically acceptable dosage forms, and processes for its preparation.

The drug compound having the adopted name enzalutamide, has a chemical name 4-(3-(4-cyano-3-(trifluoromethyl)phenyl)-5,5-dimethyl-4-oxo-2-thioxoimidazolidin-1-yl)-2-fluoro-N-methylbenzamide, and is represented by structure of formula I.

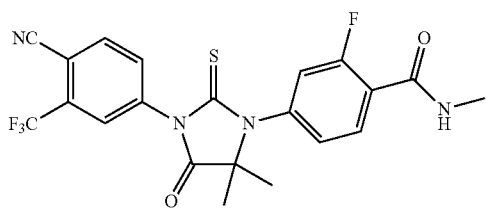

Formula I

Enzalutamide is an oral, once-daily investigational agent that is an androgen receptor signaling inhibitor used for the potential treatment of men with castration-resistant prostate cancer previously treated with docetaxel-based chemotherapy. Enzalutamide inhibits androgen receptor signaling in three distinct ways: it inhibits 1) testosterone binding to androgen receptors; 2) nuclear translocation of androgen receptors; and 3) DNA binding and activation by androgen receptors. U.S. Pat. No. 7,709,517 discloses enzalutamide, method of use and it's pharmaceutically composition.

The occurrence of different polymorphs is possible for some compounds. A single compound may give rise to a variety of solid forms having distinct physical properties. This variation in solid forms may be significant and may result in differences in pharmaceutical products with respect to solubility, bioavailability, stability and other properties. Because polymorphic forms can vary in their physical properties, regulatory authorities require that efforts shall be made to identify all polymorphic forms, e.g., crystalline, amorphous, solvated, etc., of new drug substances.

The existence and possible number of polymorphic forms for a given compound cannot be predicted, and there are no "standard" procedures that can be used to prepare polymorphic forms of a substance. However, new forms of a pharmaceutically useful compound may provide an opportunity to improve the performance characteristics of pharmaceutical products. For example, in some cases, different forms of the same drug can exhibit very different solubility and dissolution rates. The discovery of new polymorphic forms enlarges selection of materials with which formulation scientists can design a pharmaceutically acceptable dosage form of a drug with a targeted release profile or other desired characteristics. Therefore, there remains a need for preparing new and stable polymorphic forms of enzalutamide.

SUMMARY OF THE INVENTION

In an aspect, the present application provides crystalline enzalutamide Form R1 characterized by its powder X-ray diffraction (PXRD) pattern having one or more peaks at about 12.3±0.2, 13.1±0.2, 15.0±0.2, and 17.5±0.2 degrees 2-theta.

In an aspect, the present invention provides crystalline enzalutamide Form R1 further characterized by the powder X-ray diffraction pattern having one or more additional peaks at about 9.8±0.2, 13.5±0.2, 14.3±0.2, 16.7±0.2, 18.9±0.2, 21.1±0.2, 21.8±0.2, 22.8±0.2 and 24.4±0.2 degrees 2-theta.

In an aspect, the present invention provides crystalline form R1 of enzalutamide characterized by a PXRD pattern substantially as illustrated by FIG. 1.

In an aspect, the present application provides a process for the preparation of crystalline enzalutamide Form R1, comprising:
a) providing a solution of enzalutamide in a solvent; and
b) isolating crystalline enzalutamide Form R1.

In an aspect, the present application provides crystalline enzalutamide Form R2 characterized by its powder X-ray diffraction (PXRD) pattern having one or more peaks at about 4.8±0.2, 11.3±0.2 and 20.2±0.2 degrees 2-theta.

In an aspect, the present invention provides crystalline enzalutamide Form R2 further characterized by the powder X-ray diffraction pattern having one or more additional peaks at about 9.7±0.2, 14.5±0.2, 15.6±0.2, 16.9±0.2 and 25.5±0.2 degrees 2-theta.

In an aspect, the present invention provides crystalline form R2 of enzalutamide characterized by a PXRD pattern substantially as illustrated by FIG. 2.

In an aspect, the present application provides a process for the preparation of crystalline enzalutamide Form R2, comprising:
a) providing a solution of enzalutamide in methanol or formic acid; and
b) isolating crystalline enzalutamide Form R2.

In an aspect, the present application provides an amorphous form of enzalutamide.

In an aspect, the present application provides a process for the preparation of amorphous form of enzalutamide, comprising:
a) providing a solution of enzalutamide in a solvent; and
b) isolating amorphous form of enzalutamide.

In an aspect, the present application provides solid dispersion comprising enzalutamide, together with one or more pharmaceutically acceptable excipients.

In an aspect, the present application provides a process for preparing a solid dispersion of amorphous enzalutamide together with one or more pharmaceutically acceptable carriers, comprising
a) providing a solution of enzalutamide in combination with one or more pharmaceutically acceptable carriers, in a suitable solvent or mixture of solvents; and
b) isolating a solid dispersion of amorphous enzalutamide together with one or more pharmaceutically acceptable carriers.

In an aspect, the present application provides pharmaceutical formulations comprising crystalline Form R1, crystalline Form R2 or amorphous form of enzalutamide or mixtures thereof together with one or more pharmaceutically acceptable excipients.

DETAILED DESCRIPTION

In an aspect, the present application provides crystalline enzalutamide Form R1 characterized by its powder X-ray diffraction (PXRD) pattern having one or more peaks at about 12.3±0.2, 13.1±0.2, 15.0±0.2, and 17.5±0.2 degrees 2-theta.

In an aspect, the present invention provides crystalline enzalutamide Form R1 further characterized by the powder X-ray diffraction pattern having additional peaks at about 9.8±0.2, 13.5±0.2, 14.3±0.2, 16.7±0.2, 18.9±0.2, 21.1±0.2, 21.8±0.2, 22.8±0.2 and 24.4±0.2 degrees 2-theta.

Figure 1:
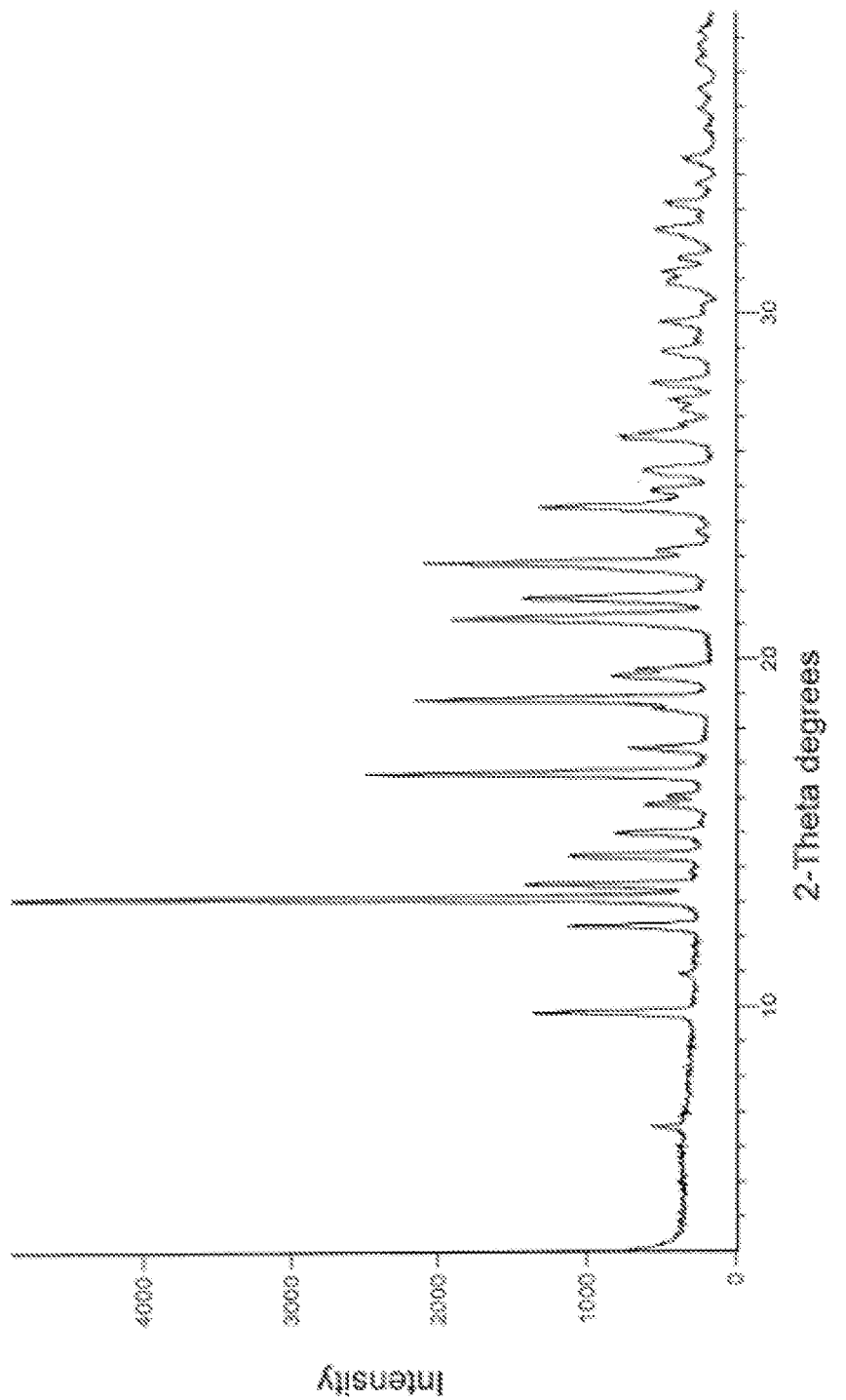
FIG. 1 illustrates the PXRD pattern of crystalline enzalutamide Form R1 obtained by the procedure of Example 1.

In an aspect, the present invention provides crystalline form R1 of enzalutamide characterized by a PXRD pattern substantially as illustrated by FIG. 1.

In an aspect, the present application provides a process for the preparation of crystalline enzalutamide Form R1, comprising:
  a) providing a solution of enzalutamide in a solvent; and
  b) isolating crystalline enzalutamide Form R1.
  Providing a solution in step a) includes:
  i) direct use of a reaction mixture containing enzalutamide that is obtained in the course of its synthesis; or
  ii) dissolving enzalutamide in a solvent.

Any physical form of enzalutamide may be utilized for providing the solution of enzalutamide in step a). Optionally, when a hydrate of enzalutamide is used, before or after step a) a water reduction or removal step may be carried out by the techniques known in the art such as distillation, heating, slurrying in a suitable solvent and the like.

In embodiments, enzalutamide obtained in the course of its synthesis can be dissolved in any suitable solvent. Examples of such suitable solvents include, but are not limited to: alcohols, such as $C_2$-$C_6$ alcohols like ethanol, 1-propanol, 2-propanol (isopropyl alcohol), 1-butanol, 2-butanol, t-butyl alcohol; or nitriles, such as acetonitrile or propionitrile, amides such as N,N-dimethylformamide, N,N-dimethylacetamide, N-methyl-2-pyrrolidone, sulfoxides such as dimethylsulfoxide, halogenated hydrocarbons such as dichloromethane, aromatic hydrocarbons such as toluene, xylene, esters such as ethyl acetate, n-propyl acetate, n-butyl acetate, isopropyl acetate, isobutyl acetate, t-butyl acetate; ethers such as diethyl ether, diisopropyl ether, methyl t-butyl ether, tetrahydrofuran, 1,4-dioxane, 2-methoxyethanol, anisole, ketones such as acetone, ethyl methyl ketone, diethyl ketone, methyl isobutyl ketone; water; or any mixtures of one or more of these solvents.

The dissolution temperatures may range from about 0° C. to about the reflux temperature of the solvent, or less than about 150° C., less than about 130° C., less than about 100° C., less than about 70° C., less than about 40° C., less than about 20° C., less than about 0° C., or any other suitable temperatures, as long as a clear solution of enzalutamide is obtained without affecting its quality. The solution may optionally be treated with carbon, flux-calcined diatomaceous earth (Hyflow) or any other suitable material to remove color, insoluble materials, improve clarity of the solution, and/or remove impurities adsorbable on such material. Optionally, the solution obtained above may be filtered to remove any insoluble particles. The insoluble particles may be removed suitably by filtration, centrifugation, decantation, or any other suitable techniques under pressure or under reduced pressure. The solution may be filtered by passing through paper, glass fiber, cloth or other membrane material, or a bed of a clarifying agent such as Celite® or Hyflow. Depending upon the equipment used and the concentration and temperature of the solution, the filtration apparatus may need to be preheated to avoid premature crystallization.

Step b) involves isolating crystalline enzalutamide Form R1 from the solution obtained in step a). Isolation of crystalline enzalutamide Form R1 in step b) is carried out by methods including cooling, crash cooling, concentrating the mass, adding an anti-solvent, adding seed crystals to induce crystallization or evaporation or the like or combinations thereof. Stirring or other alternate methods such as shaking, agitation, or the like, may also be employed for the isolation. Alternatively when crystals of Form R1 are present in the solution obtained in step (a), those crystals may act as seed crystals and Form R1 can be isolated in presence of such seed crystals of Form R1 in step (b).

Optionally, isolation may be effected by combining a suitable anti-solvent with the solution obtained in step a). Anti-solvent as used herein refers to a liquid in which enzalutamide is less soluble or poorly soluble. An anti-solvent has no adverse effect on the quality of enzalutamide and it can assist in the solidification or precipitation of the dissolved starting material. Suitable anti-solvents that may be used include, but are not limited to: water, saturated or unsaturated, linear or branched, cyclic or acyclic, $C_1$ to $C_{10}$ hydrocarbons, such as hexanes, heptane, cyclohexane, or methylcyclohexane, ethers, such as diethyl ether, diisopropyl ether, tetrahydrofuran, dioxane, or dimethoxyethane, or mixtures thereof.

Suitable temperatures for isolation may be less than about 100° C., less than about 80° C., less than about 60° C., less than about 40° C., less than about 20° C., less than about 10° C., less than about 5° C., less than about 0° C., less than about −10° C., less than about −20° C., or any other suitable temperatures.

The isolated crystalline enzalutamide Form R1 may be recovered by methods including decantation, centrifugation, evaporation, gravity filtration, suction filtration, or any other technique for the recovery of solids under pressure or under reduced pressure. The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure, as long as the enzalutamide is not degraded in quality. The drying may be carried out for any desired times until the required product quality is achieved. The dried product may optionally be subjected to a size reduction procedure to produce desired particle sizes. Milling or micronization may be performed before drying, or after the completion of drying of the product. Techniques that may be used for particle size reduction include, without limitation, ball, roller and hammer milling, and jet milling.

In an aspect, the present application provides crystalline enzalutamide Form R2 characterized by its powder X-ray diffraction (PXRD) pattern having one or more peaks at about 4.8±0.2, 11.3±0.2 and 20.2±0.2 degrees 2-theta.

In an aspect, the present invention provides crystalline enzalutamide Form R2 further characterized by the powder X-ray diffraction pattern having one or more additional peaks at about 9.7±0.2, 14.5±0.2, 15.6±0.2, 16.9±0.2 and 25.5±0.2 degrees 2-theta.

Figure 2:
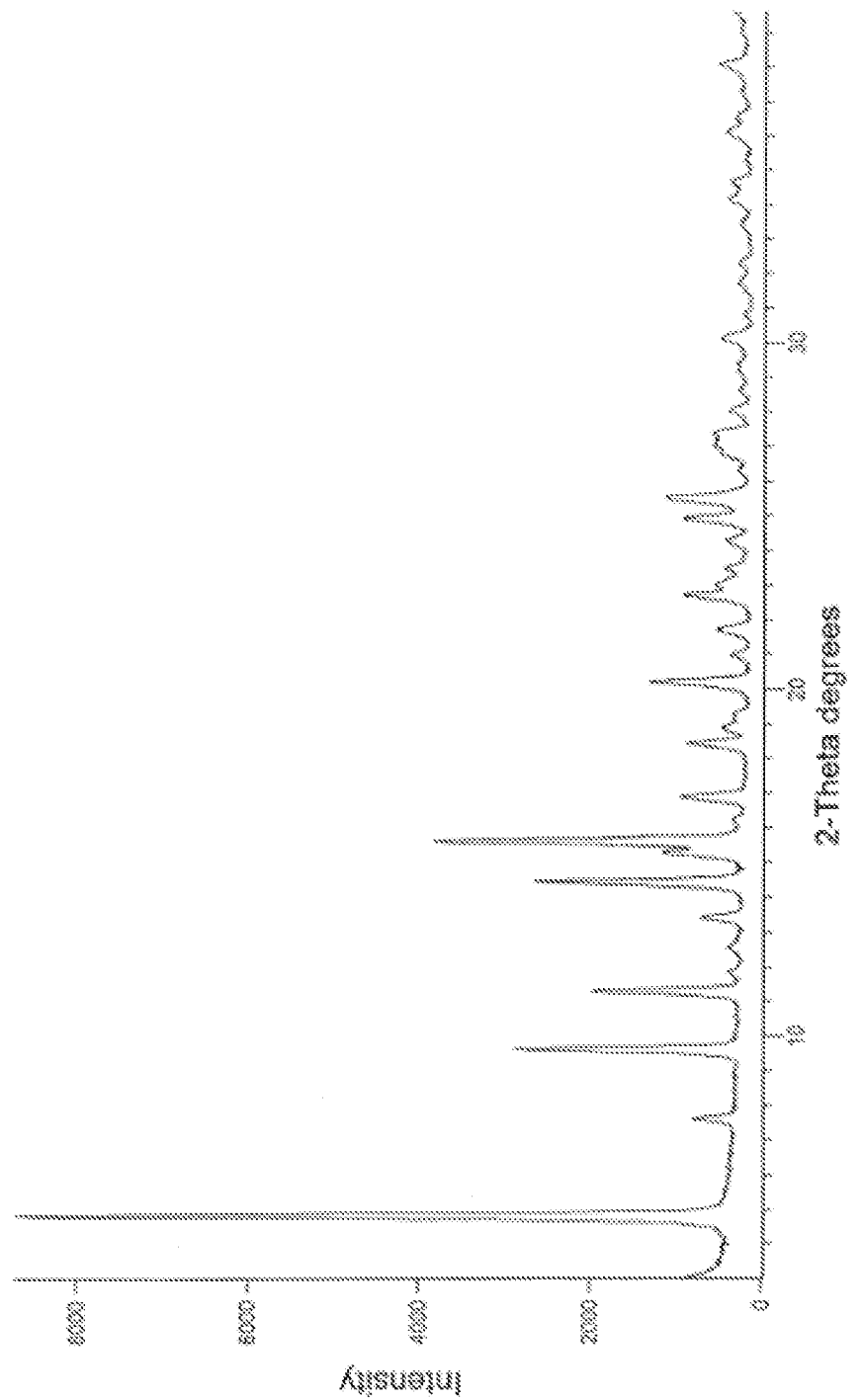
FIG. 2 illustrates the PXRD pattern of crystalline enzalutamide Form R2 obtained by the procedure of Example 26.

In an aspect, the present invention provides crystalline form R2 of enzalutamide characterized by a PXRD pattern substantially as illustrated by FIG. 2.

In an aspect, the present application provides a process for the preparation of crystalline enzalutamide Form R2, comprising:
  a) providing a solution of enzalutamide in methanol or formic acid; and
  b) isolating crystalline enzalutamide Form R2.
  Providing a solution in step a) includes:
    i) direct use of a reaction mixture containing enzalutamide that is obtained in the course of its synthesis; or
    ii) dissolving enzalutamide in methanol or formic acid.

Any physical form of enzalutamide may be utilized for providing the solution of enzalutamide in step a). Optionally, when a hydrate of enzalutamide is used, before or after step a) a water reduction or removal step may be carried out by the techniques known in the art such as distillation, heating, slurrying in a suitable solvent and the like.

In embodiments, enzalutamide obtained in the course of its synthesis can be dissolved in methanol or formic acid; or any mixtures thereof.

The dissolution temperatures may range from about 0° C. to about the reflux temperature of the solvent, or less than about 100° C., less than about 80° C., less than about 60° C., less than about 40° C., less than about 20° C., less than about 10° C., or any other suitable temperatures, as long as a clear solution of enzalutamide is obtained without affecting its quality. The solution may optionally be treated with carbon, flux-calcined diatomaceous earth (Hyflow) or any other suitable material to remove color, insoluble materials, improve clarity of the solution, and/or remove impurities adsorbable on such material. Optionally, the solution obtained above may be filtered to remove any insoluble particles. The insoluble particles may be removed suitably by filtration, centrifugation, decantation, or any other suitable techniques under pressure or under reduced pressure. The solution may be filtered by passing through paper, glass fiber, cloth or other membrane material, or a bed of a clarifying agent such as Celite® or Hyflow. Depending upon the equipment used and the concentration and temperature of the solution, the filtration apparatus may need to be preheated to avoid premature crystallization.

Step b) involves isolating crystalline enzalutamide Form R2 from the solution obtained in step a). Isolation of crystalline enzalutamide Form R2 in step b) may involve methods including cooling, concentrating the mass, adding an anti-solvent, adding seed crystals to induce crystallization or the like. Stirring or other alternate methods such as shaking, agitation, or the like, may also be employed for the isolation.

Optionally, isolation may be effected by combining a suitable anti-solvent with the solution obtained in step a). Anti-solvent as used herein refers to a liquid in which enzalutamide is less soluble or poorly soluble. An anti-solvent has no adverse effect on the quality of enzalutamide and it can assist in the solidification or precipitation of the dissolved starting material. Suitable anti-solvents that may be used include, but are not limited to: saturated or unsaturated, linear or branched, cyclic or acyclic, $C_1$ to $C_{10}$ hydrocarbons, such as hexanes, heptane, cyclohexane, or methylcyclohexane, ethers, such as diethyl ether, diisopropyl ether, tetrahydrofuran, dioxane, or dimethoxyethane, or any mixtures thereof.

Suitable temperatures for isolation may be less than about 100° C., less than about 80° C., less than about 60° C., less than about 40° C., less than about 20° C., less than about 10° C., less than about 5° C., less than about 0° C., less than about −10° C., less than about −20° C., or any other suitable temperatures.

The isolated crystalline enzalutamide Form R2 may be recovered by methods including decantation, centrifugation, gravity filtration, suction filtration, or any other technique for the recovery of solids under pressure or under reduced pressure. The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure, as long as the enzalutamide is not degraded in quality. The drying may be carried out for any desired times until the required product quality is achieved. The dried product may optionally be subjected to a size reduction procedure to produce desired particle sizes. Milling or micronization may be performed before drying, or after the completion of drying of the product. Techniques that may be used for particle size reduction include, without limitation, ball, roller and hammer milling, and jet milling.

In an aspect, the present application provides a process for the preparation of amorphous form of enzalutamide, comprising:
  a) providing a solution of enzalutamide in a solvent; and
  b) isolating amorphous form of enzalutamide.
  Providing a solution of enzalutamide in step a) includes:
    i) direct use of a reaction mixture containing enzalutamide that is obtained in the course of its synthesis; or
    ii) dissolving enzalutamide in a solvent.

Any physical form of enzalutamide may be utilized for providing the solution of enzalutamide in step a). The dissolution temperatures may range from about 0° C. to about the reflux temperature of the solvent, or less than about 60° C., less than about 50° C., less than about 40° C., less than about 30° C., less than about 20° C., less than about 10° C., or any other suitable temperatures, as long as a clear solution of enzalutamide is obtained without affecting its quality. The solution may optionally be treated with carbon, flux-calcined diatomaceous earth (Hyflow) or any other suitable material to remove color, insoluble materials, improve clarity of the solution, and/or remove impurities adsorbable on such material. Optionally, the solution obtained above may be filtered to remove any insoluble particles. The insoluble particles may be removed suitably by filtration, centrifugation, decantation, or any other suitable techniques under pressure or under reduced pressure. The solution may be filtered by passing through paper, glass fiber, cloth or other membrane material, or a bed of a clarifying agent such as Celite® or Hyflow. Depending upon the equipment used and the concentration and temperature of the solution, the filtration apparatus may need to be preheated to avoid premature crystallization.

In embodiments, enzalutamide can be dissolved in any suitable solvent. Suitable solvents include any solvents that have no adverse effect on the compound and can dissolve the starting material to a useful extent. Examples of such solvents include, but are not limited to: ethers, such as diethyl ether, diisopropyl ether, tetrahydrofuran, dioxane, or dimethoxyethane, ketones, such as acetone, methyl ethyl ketone, methyl isobutyl ketone, or diethyl ketone; esters, such as ethyl acetate, propyl acetate, isopropyl acetate, or butyl acetate; alcohols, such as methanol, ethanol, 1-propanol, 2-propanol (isopropyl alcohol), 2-methoxyethanol, 1-butanol, 2-butanol, iso-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, cyclohexanol, glycerol, or $C_1$-$C_6$ alcohols; nitriles, such as acetonitrile or propionitrile, amides, such as formamide, N,N-dimethylformamide, N,N-dimethylacetamide, N-methyl-2-pyrrolidone, or hexamethyl phosphoric triamide, sulfoxides, such as dimethylsulfoxide, halogenated hydrocarbons, such as dichloromethane, chloroform, carbon tetrachloride, or chlorobenzene, aromatic hydrocarbons, such as toluene; or any mixtures of two or more thereof.

Step b) involves isolating amorphous form of enzalutamide from the solution obtained in step a). Isolation of amorphous form of enzalutamide in step b) may involve methods including removal of solvent, cooling, crash cooling, concentrating the mass, evaporation, flash evaporation, simple evaporation, rotational drying, spray drying, thin-film drying, agitated nutsche filter drying, pressure nutsche filter drying, freeze-drying, adding anti-solvent, extraction with a solvent, adding seed to induce isolation, or the like. Stirring or other alternate methods such as shaking, agitation, or the like, may also be employed for the isolation. The amorphous form of enzalutamide as isolated may carry some amount of occluded mother liquor and may have higher than desired levels of impurities. If desired, this amorphous form may be washed with a solvent or a mixture of solvents to wash out the impurities.

Suitable temperatures for isolation may be less than about 120° C., less than about 80° C., less than about 60° C., less than about 40° C., less than about 30° C., less than about 20° C., less than about 10° C., less than about 0° C., less than about −10° C., less than about −40° C. or any other suitable temperatures.

Optionally, isolation may be effected by combining a suitable anti-solvent with the solution obtained in step a). Anti-solvent as used herein refers to a liquid in which enzalutamide is less soluble or poorly soluble. An inert anti-solvent has no adverse effect on the reaction and it can assist in the solidification or precipitation of the dissolved starting material. Suitable anti-solvents that may be used include, but are not limited to: saturated or unsaturated, linear or branched, cyclic or acyclic, $C_1$ to $C_{10}$ hydrocarbons, such as heptanes, cyclohexane, or methylcyclohexane, water; or any mixtures thereof.

The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure, as long as the enzalutamide is not degraded in quality. The drying may be carried out for any desired times until the required product quality is achieved. The dried product may optionally be subjected to a size reduction procedure to produce desired particle sizes. Milling or micronization may be performed before drying, or after the completion of drying of the product. Techniques that may be used for particle size reduction include, without limitation, ball, roller or hammer milling; or jet milling.

In an aspect, the present application provides amorphous solid dispersion comprising enzalutamide, together with one or more pharmaceutically acceptable excipients.

In an aspect, the present application provides a process for preparing a solid dispersion of amorphous enzalutamide together with one or more pharmaceutically acceptable carriers, comprising
  a) providing a solution of enzalutamide in combination with one or more pharmaceutically acceptable carrier, in a suitable solvent or mixture of solvents;
  b) isolating a solid dispersion of amorphous enzalutamide together with one or more pharmaceutically acceptable carriers.

Step a) involves providing a solution of enzalutamide in combination with at least one pharmaceutically acceptable carrier, in a suitable solvent or mixture of solvents;

Step a) may involve forming a solution of enzalutamide together with one or more pharmaceutically acceptable carriers. In embodiments, a carrier enhances stability of the amorphous solid upon removal of solvent.

Providing the solution in step a) includes:
  i) direct use of a reaction mixture containing enzalutamide that is obtained in the course of its manufacture, if desired, after addition of one or more pharmaceutically acceptable carriers; or
  ii) dissolution of enzalutamide in a suitable solvent, either alone or in combination with one or more pharmaceutically acceptable carriers.

Any physical form of enzalutamide, such as crystalline, amorphous or their mixtures may be utilized for providing a solution in step a).

Pharmaceutically acceptable carriers that may be used in step a) include, but are not limited to: diluents such as starches, pregelatinized starches, lactose, powdered celluloses, microcrystalline celluloses, dicalcium phosphate, tricalcium phosphate, mannitol, sorbitol, sugar, or the like; binders such as acacia, guar gum, tragacanth, gelatin, polyvinylpyrrolidones, hydroxypropyl celluloses, hydroxypropyl methyl celluloses, pregelatinized starches, or the like; disintegrants such as starches, sodium starch glycolate, pregelatinized starches, crospovidones, croscarmellose sodium, colloidal silicon dioxide, or the like; lubricants such as stearic acid, magnesium stearate, zinc stearate, or the like; glidants such as colloidal silicon dioxide or the like; solubility or wetting enhancers such as anionic or cationic or neutral surfactants; complex forming agents such as various grades of cyclodextrins or resins; release rate controlling agents such as hydroxypropyl celluloses, hydroxymethyl celluloses, hydroxypropyl methylcelluloses, ethylcelluloses, methylcelluloses, various grades of methyl methacrylates, waxes, or the like. Other pharmaceutically acceptable excipients that are of use include, but are not limited to, film formers, plasticizers, colorants, flavoring agents, sweeteners, viscosity enhancers, preservatives, antioxidants, or the like.

The dissolution temperatures may range from about 0° C. to about the reflux temperature of the solvent, or less than about 60° C., less than about 50° C., less than about 40° C., less than about 30° C., less than about 20° C., less than about 10° C., or any other suitable temperatures, as long as a clear solution of enzalutamide is obtained without affecting its quality. The solution may optionally be treated with carbon, flux-calcined diatomaceous earth (Hyflow) or any other suitable material to remove color, insoluble materials, improve clarity of the solution, and/or remove impurities adsorbable on such material. Optionally, the solution obtained above may be filtered to remove any insoluble particles. The insoluble particles may be removed suitably by filtration, centrifugation, decantation, or any other suitable techniques under pressure or under reduced pressure. The solution may be filtered by passing through paper, glass fiber, cloth or other membrane material, or a bed of a clarifying agent such as Celite® or Hyflow. Depending upon the equipment used and the concentration and temperature of the solution, the filtration apparatus may need to be preheated to avoid premature crystallization.

Suitable solvents that may be used in step a) include but are not limited to: ethers, such as diethyl ether, diisopropyl ether, tetrahydrofuran, dioxane, or dimethoxyethane, ketones, such as acetone, methyl ethyl ketone, methyl isobutyl ketone, or diethyl ketone; esters, such as ethyl acetate, propyl acetate, isopropyl acetate, or butyl acetate; alcohols, such as methanol, ethanol, 2-nitroethanol, 2-fluoroethanol, ethylene glycol, 1-propanol, 2-propanol (isopropyl alcohol), 2-methoxyethanol, 1-butanol, 2-butanol, iso-butyl alcohol, t-butyl alcohol, 2-ethoxyethanol, neo-pentyl alcohol, t-pentyl alcohol, diethylene glycol monomethyl ether, cyclohexanol, or $C_1$-$C_6$ alcohols; nitriles, such as acetonitrile or propionitrile, amides, such as formamide, N,N-dimethylformamide, N,N-dimethylacetamide, N-methyl-2-pyrrolidone, or hexamethyl phosphoric triamide, sulfoxides, such as dimethylsulfoxide, halogenated hydrocarbons, such as dichloromethane, chloroform, carbon tetrachloride, or chlorobenzene, aromatic hydrocarbons, such as toluene; or any mixtures of two or more thereof.

Step b) involves isolating a solid dispersion of amorphous enzalutamide together with one or more pharmaceutically acceptable carriers. Isolation of solid dispersion of amorphous form of enzalutamide in step b) may involve methods including removal of solvent, cooling, crash cooling, concentrating the mass, evaporation, flash evaporation, simple evaporation, rotational drying, spray drying, thin-film drying, agitated nutsche filter drying, pressure nutsche filter drying, freeze-drying, adding anti-solvent, extraction with a solvent, adding seed to induce isolation, or the like. Stirring or other alternate methods such as shaking, agitation, or the like, may also be employed for the isolation. The amorphous form of enzalutamide as isolated may carry some amount of occluded mother liquor and may have higher than desired levels of impurities. If desired, this amorphous form may be washed with a solvent or a mixture of solvents to wash out the impurities.

Suitable temperatures for isolation may be less than about 120° C., less than about 80° C., less than about 60° C., less than about 40° C., less than about 30° C., less than about 20° C., less than about 10° C., less than about 0° C., less than about −10° C., less than about −40° C. or any other suitable temperatures.

Optionally, isolation may be effected by combining a suitable anti-solvent with the solution obtained in step a). Anti-solvent as used herein refers to a liquid in which enzalutamide is less soluble or poorly soluble. An inert anti-solvent has no adverse effect on the reaction and it can assist in the solidification or precipitation of the dissolved starting material. Suitable anti-solvents that may be used include, but are not limited to: saturated or unsaturated, linear or branched, cyclic or acyclic, $C_1$ to $C_{10}$ hydrocarbons, such as heptanes, cyclohexane, or methylcyclohexane, water; or any mixtures thereof.

The recovered solid may optionally be dried. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure, as long as the enzalutamide is not degraded in quality. The drying may be carried out for any desired times until the required product quality is achieved. The dried product may optionally be subjected to a size reduction procedure to produce desired particle sizes. Milling or micronization may be performed before drying, or after the completion of drying of the product. Techniques that may be used for particle size reduction include, without limitation, ball, roller or hammer milling; or jet milling.

Crystalline enzalutamide Form R1, crystalline enzalutamide Form R2, amorphous form of enzalutamide or a solid dispersion of enzalutamide together with one or more pharmaceutically acceptable excipients of the present application may be further formulated as: solid oral dosage forms such as, but not limited to: powders, granules, pellets, tablets, and capsules; liquid oral dosage forms such as but not limited to syrups, suspensions, dispersions, and emulsions; and injectable preparations such as but not limited to solutions, dispersions, and freeze dried compositions. Formulations may be in the forms of immediate release, delayed release or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared using techniques such as direct blending, dry granulation, wet granulation, and extrusion and spheronization. Compositions may be presented as uncoated, film coated, sugar coated, powder coated, enteric coated, and modified release coated. Compositions of the present application may further comprise one or more pharmaceutically acceptable excipients.

Pharmaceutically acceptable excipients that are useful in the present application include, but are not limited to: diluents such as starches, pregelatinized starches, lactose, powdered celluloses, microcrystalline celluloses, dicalcium phosphate, tricalcium phosphate, mannitol, sorbitol, sugar and the like; binders such as acacia, guar gum, tragacanth, gelatin, polyvinylpyrrolidones, hydroxypropyl celluloses, hydroxypropyl methylcelluloses, pregelatinized starches and the like; disintegrants such as starches, sodium starch glycolate, pregelatinized starches, crospovidones, croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants; complex forming agents such as various grades of cyclodextrins and resins; release rate controlling agents such as hydroxypropyl celluloses, hydroxymethyl celluloses, hydroxypropyl methylcelluloses, ethylcelluloses, methylcelluloses, various grades of methyl methacrylates, waxes and the like. Other pharmaceutically acceptable excipients that are of use include but are not limited to film formers, plasticizers, colorants, flavoring agents, sweeteners, viscosity enhancers, preservatives, antioxidants, and the like.

Polymorphic forms are characterized by scattering techniques, e.g., x-ray powder diffraction pattern, by spectroscopic methods, e.g., infra-red, $^{13}$C nuclear magnetic resonance spectroscopy, and by thermal techniques, e.g., differential scanning calorimetry or differential thermal analysis. The compound of this application is best characterized by the X-ray powder diffraction pattern determined in accordance with procedures that are known in the art. For a discussion of these techniques see J. Haleblian, *J. Pharm. Sci.* 1975 64:1269-1288, and J. Haleblian and W. McCrone, *J. Pharm. Sci.* 1969 58:911-929. Crystal forms of the application can be further processed to modulate particle size. For example, the crystal forms of the application can be milled to reduce average crystal size and/or to prepare a sample suitable for manipulation and formulation.

Generally, a diffraction angle (2θ) in powder X-ray diffractometry may have an error in the range of ±0.2°. Therefore, the aforementioned diffraction angle values should be understood as including values in the range of about ±0.2°. Accordingly, the present application includes not only crystals whose peak diffraction angles in powder X-ray diffractometry completely coincide with each other, but also crystals whose peak diffraction angles coincide with each other with an error of about ±0.2°. Therefore, in the present specification, the phrase "having a diffraction peak at a diffraction angle (2θ∟ ±0.2°) of 7.9°" means "having a diffraction peak at a diffraction angle (2θ) of 7.7° to 8.1°. Although the intensities of peaks in the x-ray powder diffraction patterns of different batches of a compound may vary slightly, the peaks and the peak locations are characteristic for a specific polymorphic form. Alternatively, the term "about" means within an acceptable standard error of the mean, when considered by one of ordinary skill in the art. The relative intensities of the XRD peaks can vary depending on the sample preparation technique, crystal size distribution, various filters used, the sample mounting procedure, and the particular instrument employed. Moreover, instrument variation and other factors can affect the 2-theta values. Therefore, the term "substantially" in the context of XRD is meant to encompass that peak assignments can vary by plus or minus about 0.2 degree. Moreover, new peaks may be observed or existing peaks may disappear, depending on the type of the machine or the settings (for example, whether a Ni filter is used or not. All PXRD data reported herein are obtained using a Bruker AXS D8 Advance Powder X-ray Diffractometer or a PANalytical X-ray Diffractometer, using copper Kα radiation.

DEFINITIONS

The following definitions are used in connection with the present application unless the context indicates otherwise. The term "anti-solvent" refers to a liquid that, when combined with a solution of enzalutamide, reduces solubility of the enzalutamide in the solution, causing crystallization or precipitation in some instances spontaneously, and in other instances with additional steps, such as aging, seeding, cooling, scratching and/or concentrating. Celite® is flux-calcined diatomaceous earth. Celite® is a registered trademark of World Minerals Inc. Hyflow is flux-calcined diatomaceous earth treated with sodium carbonate. Hyflo Super Cel™ is a registered trademark of the Manville Corp. Polymorphs are different solids having the same molecular structure, yet having distinct physical properties when compared to other polymorphs of the same structure.

An "alcohol" is an organic compound containing a carbon bound to a hydroxyl group. "$C_1$-$C_6$ alcohols" include, but are not limited to, methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, phenol, glycerol, or the like.

An "aliphatic or alicyclic hydrocarbon solvent" refers to a liquid, non-aromatic, hydrocarbon, which may be linear, branched, or cyclic. It is capable of dissolving a solute to form a uniformly dispersed solution. Examples of a hydrocarbon solvent include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, $C_5$-$C_8$ aliphatic hydrocarbons, ligroin, petroleum ethers, or mixtures thereof.

"Aromatic hydrocarbon solvent" refers to a liquid, unsaturated, cyclic, hydrocarbon containing one or more rings which has at least one 6-carbon ring containing three double bonds. It is capable of dissolving a solute to form a uniformly dispersed solution. Examples of an aromatic hydrocarbon solvent include, but are not limited to, benzene toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$ aromatic hydrocarbons, or mixtures thereof.

An "ether solvent" is an organic solvent containing an oxygen atom —O— bonded to two other carbon atoms. "Ether solvents" include but are not limited to diethyl ether, diisopropyl ether, methyl t-butyl ether, glyme, diglyme, tetrahydrofuran, 1,4-dioxane, dibutyl ether, dimethylfuran, 2-methoxyethanol, 2-ethoxyethanol, anisole, $C_{2-6}$ ethers, or the like.

An "ester" is an organic compound containing a carboxyl group —(C=O)—O— bonded to two other carbon atoms. "$C_3$-$C_6$ esters" include, but are not limited to, ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate, or the like.

A "ketone" is an organic compound containing a carbonyl group —(C=O)— bonded to two other carbon atoms. "$C_3$-$C_6$ ketones" include, but are not limited to, acetone, ethyl methyl ketone, diethyl ketone, methyl isobutyl ketone, ketones, or the like.

A "nitrile" is an organic compound containing a cyano —(C≡N) bonded to another carbon atom. "$C_2$-$C_6$ Nitriles" include, but are not limited to, acetonitrile, propionitrile, butanenitrile, or the like.

All percentages and ratios used herein are by weight of the total composition and all measurements made are at about 25° C. and about atmospheric pressure, unless otherwise designated. All temperatures are in degrees Celsius unless specified otherwise. As used herein, "comprising" means the elements recited, or their equivalents in structure or function, plus any other element or elements which are not recited. The terms "having" and "including" are also to be construed as open ended. All ranges recited herein include the endpoints, including those that recite a range "between" two values. Whether so indicated or not, all values recited herein are approximate as defined by the circumstances, including the degree of expected experimental error, technique error, and instrument error for a given technique used to measure a value.

Certain specific aspects and embodiments of the present application will be explained in greater detail with reference to the following examples, which are provided only for purposes of illustration and should not be construed as limiting the scope of the application in any manner. Reasonable variations of the described procedures are intended to be within the scope of the present invention. While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EXAMPLES

Example 1: Preparation of Crystalline Enzalutamide Form R1

Methyl 2-((3-fluoro-4-(methylcarbamoyl)phenyl)amino)-2-methylpropanoate (45 g), 4-isothiocyanato-2-(trifluoromethyl)benzonitrile (95.6 g), dimethylsulphoxide (45 mL) and isopropyl acetate (90 mL) charged into round bottom flask, heated to 85° C. and maintained at 85° C. for 16 hours. Methanol (7.5 mL) was added to the reaction mixture at 65° C. and stirred at 65-68° C. for 30 minutes. Isopropyl acetate (360 mL) and water (180 mL) was added to the reaction mixture at 20° C. and stirred for 20 minutes. Layers were separated, charcoal (4.5 g) was added to the organic layer and stirred for 15 minutes. The resultant reaction mixture was passed through celite bed and filtrate solvent was evaporated under reduced pressure at below 50° C. followed by traces of isopropyl acetate was chased with isopropyl alcohol (90 mL). To the crude compound, isopropyl alcohol (450 mL) was added, heated to 75° C. and stirred at 75° C. for 20 minutes. The resultant reaction mixture was cooled to 0° C., separated solid was collected by filtration, washed with isopropyl alcohol (2×70 mL) and dried at 50° C. for 45 minutes to afford 61 g of title compound.

The Powder X-ray diffraction (PXRD) pattern of enzalutamide obtained in above example is in accordance with FIG. 1.

Example 2: Preparation of Crystalline Enzalutamide Form R1

Methyl 2-((3-fluoro-4-(methylcarbamoyl)phenyl)amino)-2-methylpropanoate (200 g), 4-isothiocyanato-2-(trifluoromethyl)benzonitrile (425 g), dimethylsulphoxide (200 mL) and isopropyl acetate (400 mL) charged into round bottom flask, heated to 85° C. and maintained at 83° C. for 14 hours. Methanol (30 mL) was added to the reaction mixture at 65° C. and stirred at 65-67° C. for 30 minutes. Isopropyl acetate (1400 mL), water (600 mL) and isopropyl alcohol (400 mL) was added to the reaction mixture at 20° C. and stirred for 15 minutes. Layers were separated and organic layer was dried over sodium sulphate. Charcoal (20 g) was added to the organic layer and stirred for 25 minutes. The resultant reaction mixture was passed through celite bed and filtrate solvent was evaporated under reduced pressure at below 50° C. To the crude compound, isopropyl alcohol (1600 mL) was added, heated to 75° C. and stirred at 75° C. for 20 minutes. The resultant reaction mixture was cooled to 5° C., separated solid was collected by filtration, washed with isopropyl alcohol (2×300 mL) and dried at 50° C. for 45 minutes to afford 278 g of title compound.

Example 3: Preparation of Crystalline Enzalutamide Form R1

Enzalutamide (100 mg) and acetic acid (1 mL) was charged into a round bottom flask at 26° C. and stirred for 5 minutes. Water (10 mL) was added to the resultant reaction mass at 26° C. and stirred at 26° C. for 15 minutes. Separated solid was collected by filtration and dried at 50° C. under reduced pressure for 1 hour to afford the title compound.

Yield: 68 mg

Example 4: Preparation of Crystalline Enzalutamide Form R1

Enzalutamide (200 mg) and tetrahydrofuran (1 mL) was charged into a round bottom flask at 26° C. and heated to 50° C. for clear solution. The resultant reaction mass was added to the water (25 mL) at 80° C. and stirred at 80° C. for 15 minutes. Separated solid was collected by filtration and dried at 50° C. under reduced pressure for 1 hour to afford the title compound. Yield: 132 mg

Example 5: Preparation of Crystalline Enzalutamide Form R1

Enzalutamide (200 mg) and isopropyl alcohol (10 mL) was charged into a round bottom flask at 26° C. and heated to 50° C. for clear solution. The resultant reaction mass was added to the n-heptane (50 mL) at 26° C. and stirred at 26° C. for 15 minutes. Separated solid was collected by filtration and dried at 50° C. under reduced pressure for 1 hour to afford the title compound. Yield: 160 mg

Example 6: Preparation of Crystalline Enzalutamide Form R1

Enzalutamide (100 mg) acetone (2 mL) and water (2 mL) were charged into a round bottom flask at 26° C. and heated to 55° C. for clear solution. The resultant reaction mass was cooled to −2° C. and stirred at −2° C. for 15 minutes. Separated solid was collected by filtration and dried at 50° C. under reduced pressure for 30 minutes to afford the title compound. Yield: 80 mg

Example 7: Preparation of Crystalline Enzalutamide Form R1

Enzalutamide (200 mg) and ethanol (4 mL) was charged into a round bottom flask at 26° C. and heated to 65° C. for clear solution. The resultant reaction mass was cooled to 0° C. and stirred at 0° C. for 15 minutes. Separated solid was collected by filtration and dried at 50° C. under reduced pressure for 1 hour to afford the title compound.

Yield: 142 mg

Example 8: Preparation of Crystalline Enzalutamide Form R1

Enzalutamide (200 mg) and toluene (20 mL) was charged into a round bottom flask at 26° C. and heated to 90° C. for clear solution. The resultant reaction mass was cooled to 2° C. and stirred at 2° C. for 15 minutes. Separated solid was collected by filtration, washed with pre cooled (5° C.) toluene (5 mL) and dried at 50° C. under reduced pressure for 1 hour to afford the title compound. Yield: 180 mg

Example 9: Preparation of Crystalline Enzalutamide Form R1

Enzalutamide (200 mg) and methyl isopropyl ketone (6 mL) was charged into a round bottom flask at 26° C. and heated to 50° C. for clear solution. The resultant reaction mass was cooled to 0° C. and stirred at 0° C. for 15 minutes. Separated solid was collected by filtration, washed with pre cooled (0° C.) methyl isopropyl ketone (5 mL) and dried at 50° C. under reduced pressure for 1 hour to afford the title compound. Yield: 162 mg

Example 10: Preparation of Crystalline Enzalutamide Form R1

Enzalutamide (200 mg) and tetrahydrofuran (0.5 mL) was charged into a round bottom flask at 26° C. and heated to 50° C. for clear solution. The resultant reaction mass was cooled to 5° C. and stirred at 5° C. for 15 minutes. Separated solid was collected by filtration, washed with pre cooled (5° C.) tetrahydrofuran (0.5 mL) and dried at 50° C. under reduced pressure for 1 hour to afford the title compound. Yield: 90 mg

Example 11: Preparation of Crystalline Enzalutamide Form R1

Enzalutamide (200 mg) and dimethylsulphoxide (1 mL) was charged into a round bottom flask at 26° C. and heated to 50° C. for clear solution. The resultant reaction mass was added to the water (50 mL) at 26° C. and stirred at 26° C. for 15 minutes. Separated solid was collected by filtration, washed with water (10 mL) and dried at 50° C. under reduced pressure for 1 hour to afford the title compound. Yield: 185 mg

Example 12: Preparation of Crystalline Enzalutamide Form R1

Enzalutamide (200 mg) and toluene (100 mL) was charged into a round bottom flask at 26° C. and heated to 80° C. for clear solution. The resultant reaction mixture solvent was evaporated at below 90° C. under vacuum and finally dried the material in buchi rotavapor at 90° C. under vacuum for 1 hour to afford the title compound. Yield: 190 mg

Example 13: Preparation of Crystalline Enzalutamide Form R1

Enzalutamide (200 mg) and isopropyl alcohol (5 mL) was charged into a round bottom flask at 26° C. and heated to 70° C. for clear solution. The resultant reaction mass was cooled to 5° C. and stirred at 5° C. for 15 minutes. Separated solid was collected by filtration, washed with pre cooled (0° C.) isopropyl alcohol (2 mL) and dried at 50° C. under reduced pressure for 1 hour to afford the title compound. Yield: 182 mg

Example 14: Preparation of Crystalline Enzalutamide Form R1

Enzalutamide (200 mg) and n-butanol (5 mL) was charged into a round bottom flask at 26° C. and heated to 68° C. for clear solution. The resultant reaction mass was cooled to 5° C. and stirred at 5° C. for 10 minutes. Separated solid was collected by filtration, washed with pre cooled (0° C.) n-butanol (2 mL) and dried at 50° C. under reduced pressure for 1 hour to afford the title compound. Yield: 173 mg

Example 15: Preparation of Crystalline Enzalutamide Form R1

Enzalutamide (200 mg) and methyl ethyl ketone (4 mL) was charged into a round bottom flask at 26° C. and heated to 52° C. for clear solution. The resultant reaction mass was cooled to 2° C. and stirred at 2° C. for 15 minutes. Separated solid was collected by filtration, washed with pre cooled (2° C.) methyl ethyl ketone (2 mL) and dried at 50° C. under reduced pressure for 1 hour to afford the title compound. Yield: 170 mg

Example 16: Preparation of Crystalline Enzalutamide Form R1

Enzalutamide (200 mg) and acetonitrile (1 mL) was charged into a round bottom flask at 26° C. and heated to 45° C. for clear solution. The resultant reaction mass was cooled to 0° C. and stirred at 0° C. for 15 minutes. Separated solid was collected by filtration, washed with pre cooled (0° C.) acetonitrile (0.5 mL) and dried at 50° C. under reduced pressure for 1 hour to afford the title compound. Yield: 61 mg

Example 17: Preparation of Crystalline Enzalutamide Form R1

Enzalutamide (200 mg) and ethyl acetate (1 mL) was charged into a round bottom flask at 26° C. and heated to 50° C. for clear solution. The resultant reaction mass was cooled to 0° C. and stirred at 0° C. for 20 minutes. Separated solid was collected by filtration, washed with pre cooled (0° C.) ethyl acetate (0.5 mL) and dried at 50° C. under reduced pressure for 1 hour to afford the title compound. Yield: 72 mg

Example 18: Preparation of Crystalline Enzalutamide Form R1

Enzalutamide (200 mg) and n-butyl acetate (1 mL) was charged into a round bottom flask at 26° C. and heated to 50° C. for clear solution. The resultant reaction mass was cooled to 0° C. and stirred at 0° C. for 15 minutes. Separated solid was collected by filtration, washed with pre cooled (0° C.) n-butyl acetate (0.5 mL) and dried at 50° C. under reduced pressure for 1 hour to afford the title compound. Yield: 102 mg

Example 19: Preparation of Crystalline Enzalutamide Form R1

Enzalutamide (200 mg) and methyl isobutyl ketone (2 mL) was charged into a round bottom flask at 26° C. and heated to 55° C. for clear solution. The resultant reaction mass was cooled to 0° C. and stirred at 0° C. for 15 minutes. Separated solid was collected by filtration, washed with pre cooled (0° C.) methyl isobutyl ketone (1 mL) and dried at 50° C. under reduced pressure for 1 hour to afford the title compound. Yield: 120 mg

Example 20: Preparation of Crystalline Enzalutamide Form R1

Enzalutamide (200 mg) and xylene (10 mL) was charged into a round bottom flask at 26° C. and heated to 90° C. for clear solution. The resultant reaction mass was cooled to 2° C. and stirred at 2° C. for 15 minutes. Separated solid was collected by filtration, washed with pre cooled (2° C.) xylene (5 mL) and dried at 50° C. under reduced pressure for 1 hour to afford the title compound. Yield: 182 mg

Example 21: Preparation of Crystalline Enzalutamide Form R1

Enzalutamide (200 mg) and N, N-dimethylformamide (2 mL) was charged into a round bottom flask at 26° C. and heated to 40° C. for clear solution. To the resultant reaction mass water (50 mL) was added at 26° C. and stirred at 26° C. for 15 minutes. Separated solid was collected by filtration, washed with water (5 mL) and dried at 50° C. under reduced pressure for 1 hour to afford the title compound. Yield: 176 mg

Example 22: Preparation of Crystalline Enzalutamide Form R1

Enzalutamide (200 mg) and N-Methyl-2-pyrrolidone (2 mL) was charged into a round bottom flask at 26° C. and heated to 35° C. for clear solution. To the resultant reaction mass water (50 mL) was added at 26° C. and stirred at 26° C. for 15 minutes. Separated solid was collected by filtration, washed with water (5 mL) and dried at 50° C. under reduced pressure for 1 hour to afford the title compound. Yield: 160 mg

Example 23: Preparation of Crystalline Enzalutamide Form R1

Enzalutamide (200 mg) and tetrahydrofuran (2 mL) was charged into a round bottom flask at 26° C. and heated to 38° C. for clear solution. To the resultant reaction mass water (50 mL) was added at 26° C. and stirred at 26° C. for 15 minutes. Separated solid was collected by filtration, washed with water (5 mL) and dried at 50° C. under reduced pressure for 1 hour to afford the title compound. Yield: 167 mg

Example 24: Preparation of Crystalline Enzalutamide Form R1

Enzalutamide (200 mg) charged into a flask at 26° C. and heated to 205° C. for melting Enzalutamide. The resultant reaction mixture is kept at ambient temperature to afford title compound. Yield: 190 mg

Example 25: Preparation of Crystalline Enzalutamide Form R1

Enzalutamide (200 mg) and isopropyl alcohol (2 mL) was charged into a round bottom flask at 26° C. and heated to 80° C. for clear solution. The resultant reaction mass was kept at −60° C. Separated solid was collected by filtration and dried at 50° C. under reduced pressure for 1 hour to afford the title compound. Yield: 182 mg

Example 26: Preparation of Crystalline Enzalutamide Form R2

Enzalutamide (200 mg) and methanol (3 mL) were charged into a round bottom flask at 26° C. and heated to 58° C. for clear solution. The resultant reaction mass was cooled to 0° C. and stirred at 0° C. for 15 minutes. Separated solid was collected by filtration, washed with pre cooled (3° C.) methanol (1 mL) and dried at 70° C. under reduced pressure for 3 hours to afford the title compound. Yield: 182 mg The Powder X-ray diffraction (PXRD) pattern of enzalutamide obtained in above example is in accordance with FIG. 2.

Example 27: Preparation of Crystalline Enzalutamide Form R2

Enzalutamide (200 mg) and formic acid (1 mL) were charged into a round bottom flask at 26° C. and heated to 70° C. for clear solution. The resultant reaction mass was cooled to 0° C. and stirred at 0° C. for 15 minutes. Separated solid was collected by filtration, washed with pre cooled (3° C.) formic acid (0.5 mL) and dried at 70° C. under reduced pressure for 3 hours to afford the title compound. Yield: 105 mg

Example 28: Preparation of Amorphous Form of Enzalutamide

Enzalutamide (200 mg) and methanol (20 mL) were charged into a round bottom flask at 26° C. Resultant reaction mixture solvent was evaporated at below 65° C. under vacuum and finally dried the material in buchi rotavapor at 65° C. under vacuum to afford the title compound. Yield: 190 mg

Example 29: Preparation of Amorphous Form of Enzalutamide

Figure 3:
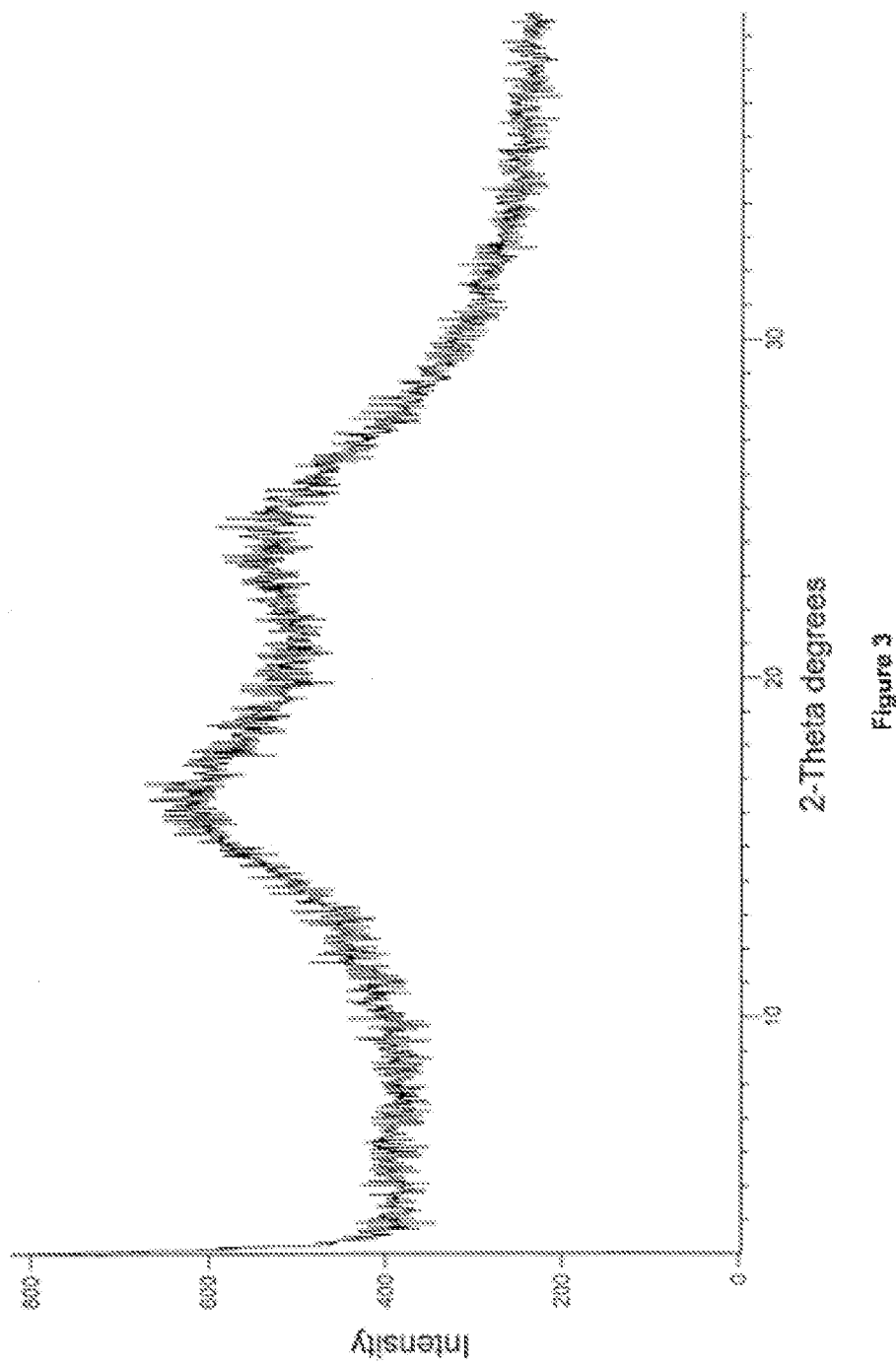
FIG. 3 illustrates the PXRD pattern of amorphous enzalutamide, obtained by the procedure of Example 29.

Enzalutamide (200 mg) and acetone (10 mL) were charged into a round bottom flask at 26° C. Resultant reaction mixture solvent was evaporated at below 50° C. under vacuum and finally dried the material in buchi rotavapor at 55° C. under vacuum to afford the title compound. Yield: 195 mg The Powder X-ray diffraction (PXRD) pattern of enzalutamide obtained in above example is in accordance with FIG. 3.

Figure 4:
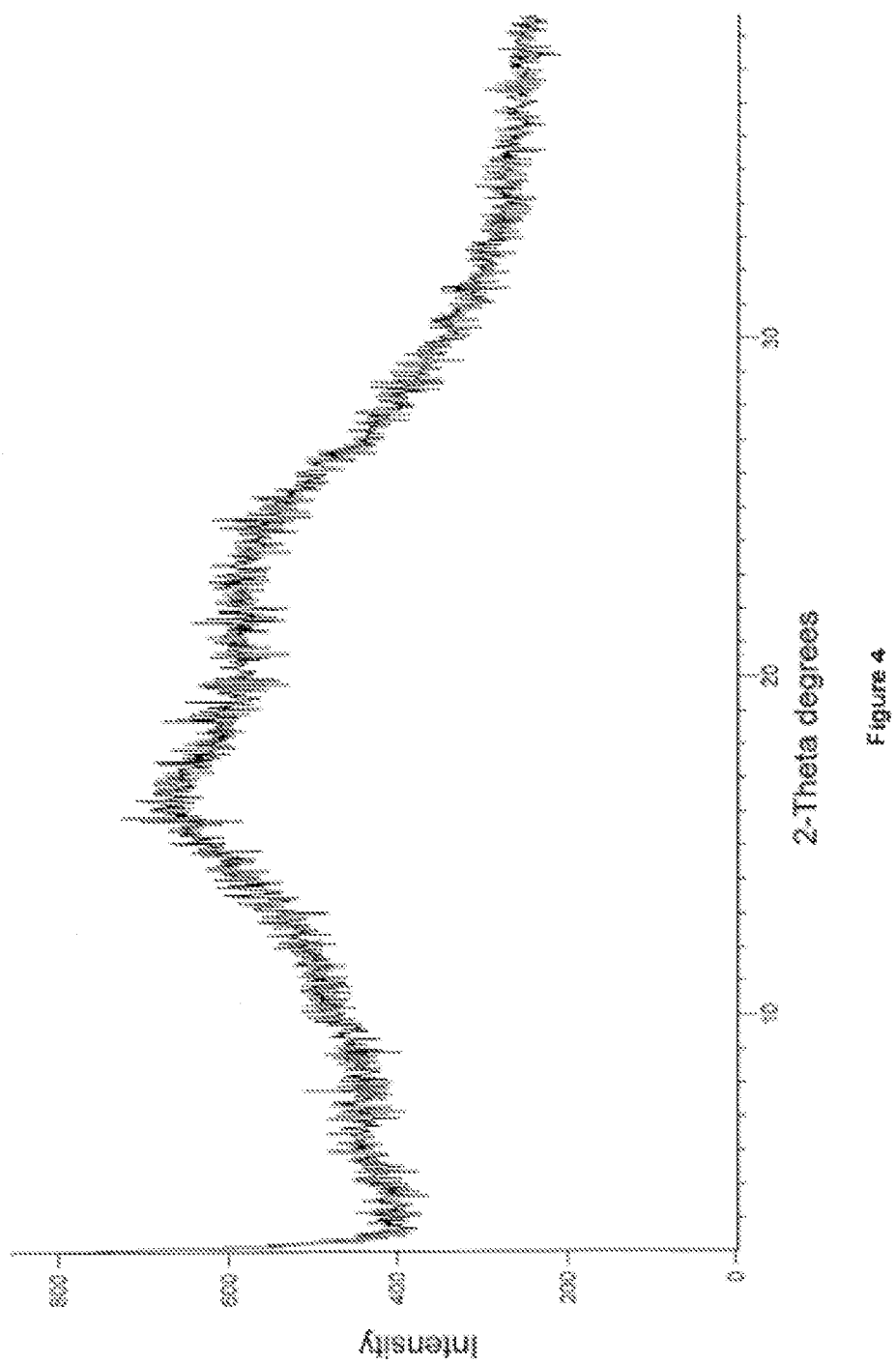
FIG. 4 illustrates the PXRD pattern of amorphous enzalutamide, obtained by the procedure of Example 30.

Example 30: Preparation of Solid Dispersion of Amorphous Enzalutamide with Polyvinylpyrrolidone Enzalutamide (200 mg), polyvinylpyrrolidone-K-90 (200 mg) and methanol (40 mL) were charged into a round bottom flask and stirred at 26° C. for 15 minutes. The resultant reaction mixture solvent was evaporated at below 55° C. under vacuum and finally dried the material in buchi rotavapor at 65° C. under vacuum to afford the title compound. Yield: 380 mg The Powder X-ray diffraction (PXRD) pattern of enzalutamide obtained in above example is in accordance with FIG. 4.

Example 31: Preparation of Crystalline Enzalutamide Form R1

Enzalutamide (500 mg) and Methanol (5 mL) were charged into a round bottom flask at 26° C. and heated to 65° C. Filtered the solution to make it particle free and filterate was cooled to 30° C. Added 25 mg seed crystals of Form R1 and stirred at 25-30° C. for 15 minutes. The reaction mixture was further cooled to 0-5° C. and stirred for 1 hour.

Separated solid was collected by filtration and dried at 70° C. under reduced pressure for 2 hours to afford the title compound. Yield: 320 mg

The invention claimed is:

1. A process for preparing crystalline form R1 of enzalutamide characterized by a powder X-ray diffraction (PXRD) pattern having peaks at 12.3±0.2, 13.1±0.2, 15.0±0.2, and 17.5±0.2 degrees 2-theta, which comprises:
   a) providing a solution of enzalutamide in a single solvent selected from the group consisting of methanol, ethanol, isopropyl alcohol, n-butanol, acetic acid, tetrahydrofuran, toluene, methyl isopropyl ketone, dimethyl sulphoxide, methyl ethyl ketone, acetonitrile, ethyl acetate, xylene, N, N-dimethyl formamide, and N-methyl-2-pyrrolidone; and
   b) isolating crystalline enzalutamide form R1.

2. The process of claim 1, wherein the isolation of crystalline form R1 in step b) is carried out by cooling, crash cooling, concentrating, adding an anti-solvent, and evaporation.

3. The process of claim 1, wherein the single solvent is methanol.

4. The process of claim 1, wherein the single solvent is isopropyl alcohol.

5. The process of claim 2, wherein the anti-solvent is selected from water or n-heptane.

\* \* \* \* \*